(12) United States Patent
Kose et al.

(10) Patent No.: US 11,278,366 B2
(45) Date of Patent: Mar. 22, 2022

(54) METHOD FOR CONTROLLING A FLEXIBLE MANIPULATOR

(71) Applicant: Canon U.S.A. Inc., Melville, NY (US)

(72) Inventors: Hidekazu Kose, Tokyo (JP); Kiyoshi Takagi, Tokyo (JP)

(73) Assignee: Canon U.S.A., Inc., Melville, NY (US)

( * ) Notice: Subject to any disclaimer, the term of this patent is extended or adjusted under 35 U.S.C. 154(b) by 421 days.

(21) Appl. No.: 15/959,800

(22) Filed: Apr. 23, 2018

(65) Prior Publication Data

US 2018/0311006 A1 Nov. 1, 2018

Related U.S. Application Data

(60) Provisional application No. 62/490,907, filed on Apr. 27, 2017.

(51) Int. Cl.
*A61B 34/00* (2016.01)
(52) U.S. Cl.
CPC .............. *A61B 34/74* (2016.02); *A61B 34/71* (2016.02); *A61B 2034/742* (2016.02)
(58) Field of Classification Search
CPC .... A61B 34/71; A61B 34/74; A61B 2034/742
See application file for complete search history.

(56) References Cited

U.S. PATENT DOCUMENTS 4,686,963 A 8/1987 Cohen et al.
5,469,254 A 11/1995 Konomura
(Continued)

FOREIGN PATENT DOCUMENTS

EP 659387 A2 6/1995
EP 2289592 A2 3/2011
(Continued)

OTHER PUBLICATIONS

Butler, E. J., et al, "Robotic Neuro-Endoscope with Concentric Tube Augmentation", IEEE/RSJ International Conference on Intelligent Robots and Systems, Oct. 7-12, 2012, pp. 2941-2946.
(Continued)

*Primary Examiner* — Rachid Bendidi
(74) *Attorney, Agent, or Firm* — Canon U.S.A., Inc., IP Division

(57) ABSTRACT

The present application relates to a flexible manipulator including at least one flexible member (bend) controlled by an input device in the form of a joystick. Specifically, to prevent the flexible manipulator inserted into a narrow space from contacting surrounding objects, the flexible manipulator according to the present invention is configured to maintain the shape when the operator releases the joystick. However, when the flexible manipulator is shaped to be at a target position and subsequently needs to be returned to the original shape, the operator manipulates the joystick using complicated and time consuming manipulation techniques. A control device in communication with the flexible manipulator is configured to allow the operator to select an input method for maintaining the shape of the flexible manipulator after the joystick is released. In addition, an input method for returning the flexible manipulator to the original shape may be selected. This enables the operator to use an appropriate input method in accordance with the purpose of a medical procedure.

23 Claims, 10 Drawing Sheets

(56) References Cited

U.S. PATENT DOCUMENTS

| | | |
|---|---|---|
| 6,858,005 B2 | 2/2005 | Ohline et al. |
| 7,591,783 B2 | 9/2009 | Boulais et al. |
| 7,744,608 B2 | 6/2010 | Lee et al. |
| 7,785,252 B2 | 8/2010 | Danitz et al. |
| 7,850,642 B2 | 12/2010 | Moll et al. |
| 7,974,681 B2 | 7/2011 | Wallace et al. |
| 8,021,326 B2 | 9/2011 | Moll et al. |
| 8,114,097 B2 | 2/2012 | Brock et al. |
| 8,306,656 B1 | 11/2012 | Schaible et al. |
| 8,332,072 B1 | 12/2012 | Schaible et al. |
| 8,348,861 B2 | 1/2013 | Glozman et al. |
| 8,372,019 B2 | 2/2013 | Golderberg et al. |
| 8,394,054 B2 | 3/2013 | Wallace et al. |
| 8,409,136 B2 | 4/2013 | Wallace et al. |
| 8,444,549 B2 | 5/2013 | Viola et al. |
| 8,668,638 B2 | 3/2014 | Donhowe et al. |
| 8,915,841 B2 | 12/2014 | Naito |
| 8,930,027 B2 | 1/2015 | Schaible et al. |
| 9,144,370 B2 | 9/2015 | Kato et al. |
| 9,333,650 B2 | 5/2016 | Bajo et al. |
| 9,404,734 B2 | 8/2016 | Ramamurthy et al. |
| 9,498,601 B2 | 11/2016 | Tanner et al. |
| 9,539,726 B2 | 1/2017 | Simaan et al. |
| 9,549,720 B2 | 1/2017 | Simaan et al. |
| 9,591,964 B2 | 3/2017 | Choset et al. |
| 9,629,688 B2 | 8/2017 | Robert et al. |
| 9,737,687 B2 | 8/2017 | Armand et al. |
| 2003/0045778 A1 | 3/2003 | Ohline et al. |
| 2004/0138525 A1 | 7/2004 | Saddat et al. |
| 2005/0131279 A1 | 6/2005 | Boulais et al. |
| 2006/0181417 A1* | 8/2006 | Pullmann ........... H03K 17/9502 340/545.2 |
| 2007/0219581 A1 | 9/2007 | Dohi et al. |
| 2008/0039715 A1 | 2/2008 | Wilson et al. |
| 2008/0221592 A1 | 9/2008 | Kawai |
| 2008/0281293 A1 | 11/2008 | Peh et al. |
| 2008/0287741 A1 | 11/2008 | Ostrovsky et al. |
| 2010/0010298 A1 | 1/2010 | Bakos et al. |
| 2011/0257480 A1 | 10/2011 | Takahashi et al. |
| 2011/0282154 A1* | 11/2011 | Umemoto ............... A61B 5/065 600/152 |
| 2012/0046522 A1 | 2/2012 | Naito |
| 2012/0078053 A1 | 3/2012 | Phee et al. |
| 2012/0136381 A1 | 5/2012 | Morrison et al. |
| 2012/0271109 A1 | 10/2012 | Belson |
| 2013/0165945 A9 | 6/2013 | Roelle et al. |
| 2015/0164596 A1 | 6/2015 | Romo et al. |
| 2017/0095298 A1* | 4/2017 | Vakharia .......... A61B 17/07207 |
| 2017/0304014 A1 | 10/2017 | Au et al. |
| 2018/0192854 A1* | 7/2018 | Hata ..................... A61B 34/30 |

FOREIGN PATENT DOCUMENTS

| | | |
|---|---|---|
| EP | 2471437 A1 | 7/2012 |
| WO | 2007/141784 A2 | 12/2007 |
| WO | 2012/054829 A2 | 4/2012 |
| WO | 2013/026012 A1 | 2/2013 |
| WO | 2014/134475 A1 | 9/2014 |
| WO | 2017/003468 A1 | 1/2017 |

OTHER PUBLICATIONS

Camarillo, D.B., et al, "Configuration Tracking for Contiuum Manipulators with Coupled Tendon Drive", IEEE Transactions on Robotics, Aug. 2009, pp. 798-808, vol. 25, No. 4, with Abstract.

Chiang, L.S., et al, "Tendon Sheath Analysis for Estimation of Distal End Force and Elongation", IEEE/ASME International Conference on Advanced Intelligent Mechatroincs, Jul. 14-17, 2009, pp. 332-337.

Hannan, M.W. et al, "Kinematics and the Implementation of an Elephant's Trunk Manipulator and Other Continuum Style Robots", Journal of Robotic Systems, 2003, pp. 45-63, vol. 20, No. 2.

Jones, B.A et al, "Kinematics for Multisection Continuum Robots", IEEE Transactions on Robotics, Feb. 2006, pp. 43-55, vol. 22, No. 1.

Kato, T. et al, "Multi-section continuum robot for endoscopic surgical clipping of intracranial aneurysms", Med Image Comput Comput Assist Interv., 2013, pp. 364-371, vol. 16, No. 0 1.

Neppalli, S., et al, "Closed-Form Inverse Kinematics for Continuum Manipulators", Advanced Robotics, 2009, pp. 2077-2091, vol. 23.

Phee, S.J., et al, "Tendon sheath analysis for estimation of distal end force and enlongation for sensorless distal end", Robotics, 2010, Cambridge University Press.

Webster, R. J. et al, "Design and Kinematic Modeling of Constant Curvature Continuum Robots: A Review", The International Journal of Robotics Research, 2010, pp. 1661-1683, vol. 29, No. 13.

Yoon, H., et al, "Active Bending Endoscopy Robot System for Navigation through Sinus Area", IEEE/RSJ International Conference on Intelligent Robots and Systems, Sep. 25-30, 2011, pp. 967-972.

Yoshimitsu, K. et al, "A novel four-wire-driven robotic catheter for radio-frequency ablation treatment", Int J Comput Assist Radiol Surg., Sep. 2014, pp. 867-874, vol. 9, No. 5.

* cited by examiner

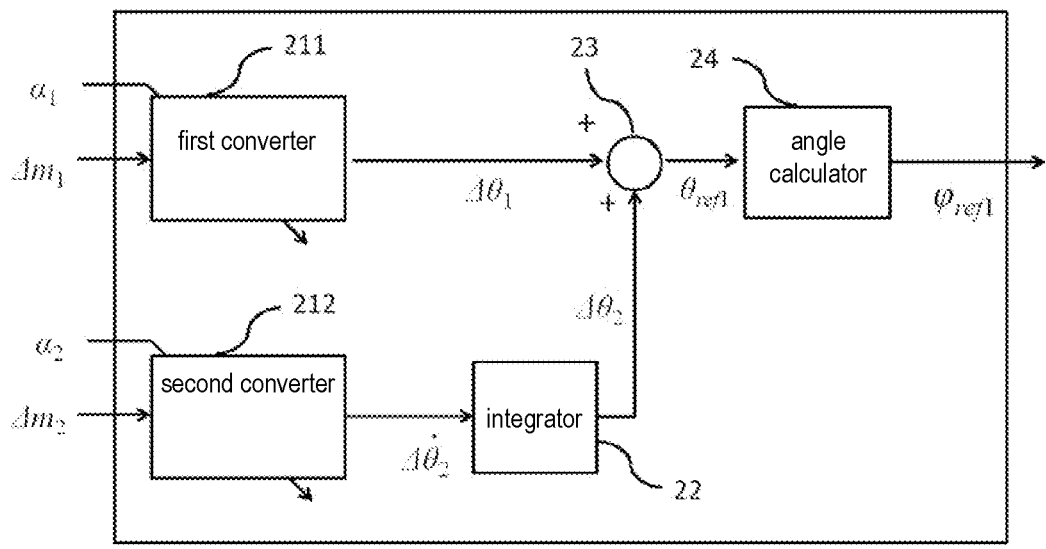
FIG. 5
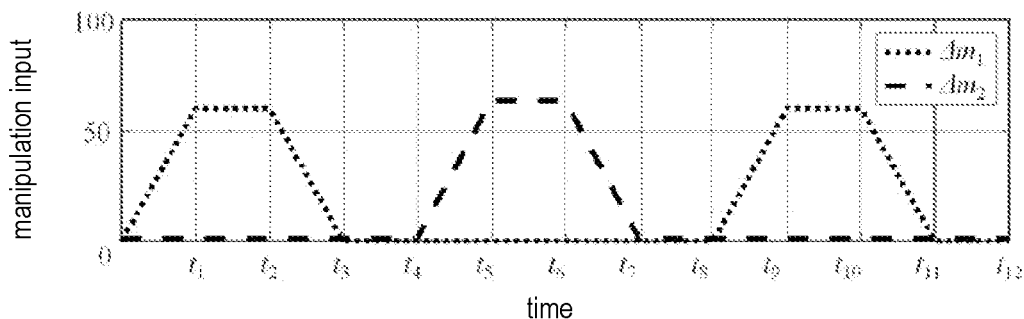
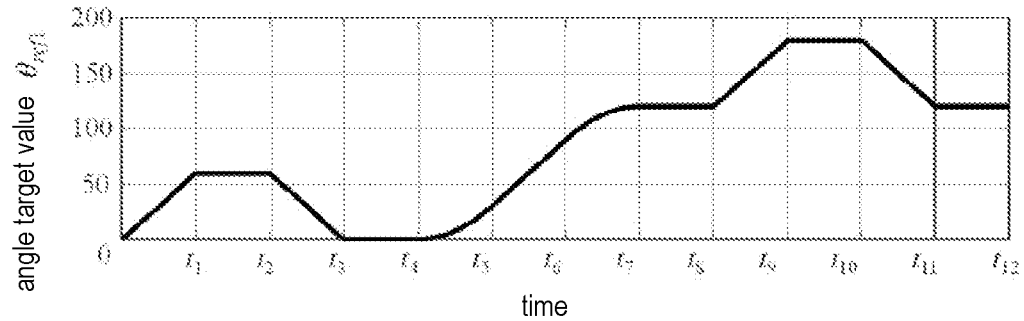
FIGs. 6A-B

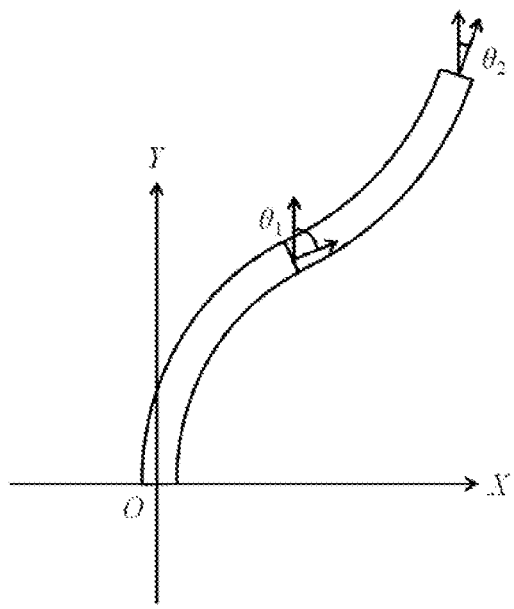
FIG. 13
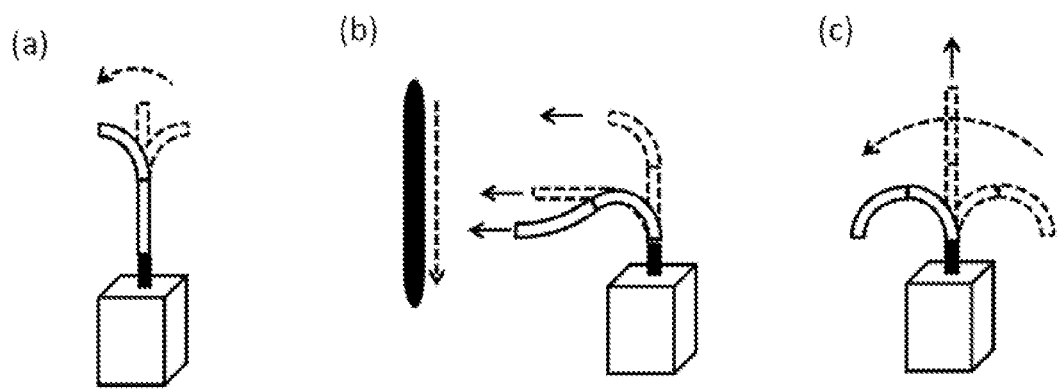
FIGs. 14A-C

METHOD FOR CONTROLLING A FLEXIBLE MANIPULATOR

CROSS-REFERENCE TO RELATED APPLICATIONS

This application claims the benefit of U.S. Provisional Patent Application Ser. No. 62/490,907, filed on Apr. 27, 2017, which is incorporated herein by reference in its entirety.

BACKGROUND

1. Field of the Invention

The present invention relates to a method and system for controlling a flexible manipulator. Specifically, the flexible manipulator is operated by using input and control devices.

2. Discussion of the Background

Minimally invasive surgeries and diagnostic procedures limit the size of incisions needed. In addition, these procedures lessen wound healing time, associated pain, and risk of infection. Laparoscopic surgery using an endoscope is a representative example of minimally invasive medical procedures. Endoscopes used in minimally invasive medical procedures can be broadly divided into hard and flexible endoscopes. A hard endoscope can obtain a clear image, but has a disadvantage that a direction from which observation can be made is limited. In addition, when the hard endoscope is inserted into a bending organ such as the esophagus, the large intestine, or a lung, an insertion portion thereof presses the organ and hurts the patient. The insertion portion of an endoscope is formed of a bendable material and thereby enables observing a wide range of locations by adjusting the angle at which the end of the endoscope is bent. An endoscope with increased number of bendable portions can reach deep into the body without contact with surrounding tissues even when the passage complexly bends. Accordingly, there is a need for development of endoscopes including at least one bendable portion that can be easily controlled and manipulated by a physician (operator).

A diagnostic procedure or surgery using an endoscope requires manipulation skills from a physician. Specifically, the physician cannot directly observe the shape (configuration) of the insertion portion of the endoscope, and it is difficult for the physician to grasp the relationship between the direction of manipulation and the direction of image observation. In particular, the shape of the insertion portion changes and the difficulty of manipulation increase with the number of bends. This increases the duration of the medical procedure and the burden on the physician and the patient.

A PCT Patent Application No. WO2017/003468 to Hata et al. filed on Jun. 30, 2015 relates to a method and apparatus for controlling a flexible manipulator including a plurality of flexible members (bends) and is incorporated herein by reference in its entirety. According to WO2017/003468, an operator selects a movement pattern of the flexible manipulator that matches the purpose of a medical procedure from among predetermined movement patterns. A controller calculates driving amount required to realize the selected movement pattern. Thus, the operator only provides a simple manipulation to realize the movement pattern. The controller disclosed in WO2017/003468 changes the current shape of a bend by an amount proportional to the input from the operator. Accordingly, when the shape of the bend is changed to a different shape and the manipulation input is subsequently set to zero, the bend maintains the changed shape. For this reason, when observation is made at a target location and the bend subsequently returns to the original shape, the manipulation system disclosed in WO2017/003468 is complicated and takes a substantial amount of time for the return manipulation. Accordingly, a method and system is required to control the shape of one or more bends of a flexible manipulator through one or more operator inputs in an efficient manner.

SUMMARY OF THE INVENTION

The present invention relates to a flexible manipulator having at least one flexible member (hereinafter can be referred to as bend, bendable portion, or flexible portion) controlled by a control device based on input provided by an operator through an input device.

In one aspect of the invention, a system and a method for manipulating a flexible member of a flexible manipulator are provided. Specifically, the flexible member is connected to a drive transmission mechanism. The input device includes a first manipulation element to input a first variable changing over time and a second manipulation element to input a second variable changing over time. The control device includes an integrator that time-integrates the second variable and an adder that adds the output of the integrator and the first variable with different coefficients. Thus, a driving amount is calculated to apply to the drive transmission mechanism. A drive source applies a driving force to the drive transmission mechanism based on the calculated driving amount to bend the flexible member.

In one embodiment, at least one of the first manipulation element and the second manipulation element of the input device includes a homing (return to origin) mechanism, which is a mechanism to return the manipulation element to the original position ("zero," "home," or "neutral" position as shown in FIG. 4) corresponding to zero input from the operator. In yet another embodiment, the transmission mechanism includes a wire that is wound around an output shaft of the drive source. Rotation of the drive source causes the wire to be pulled and the flexible member to bend. In some embodiments, the driving amount is proportional to a bend angle θ formed between the flexible member and a vertical axis, $\theta = \alpha_1 \Delta m_1 + \alpha_2 \int \Delta m_2 dt$, where $\Delta m_1(t)$ is the first variable and $\Delta m_2(t)$ is the second variable. In one embodiment, the input device includes a switch that invalidates an input from at least one of the first manipulation element and the second manipulation element. The input device may further include a third manipulation element that inputs a third variable. The first manipulation element or the third manipulation element may include the homing mechanism. In some embodiments, the adder of the control device adds the first variable and the third variable. By way of example and without limitation, the first and second manipulation element may comprise a joystick. The input device may further include dials to input coefficients to multiply the first and second variables.

In another aspect of the invention, a manipulator system comprising a plurality of flexible members, a plurality of drive sources, an input device, and a control device is provided. Specifically, each of the plurality of flexible members is connected to one of the plurality of drive transmission mechanisms. A plurality of drive sources applies a driving force to the plurality of drive transmission mechanisms. The input device includes a first manipulation element that inputs a first variable, a first selecting element that selects a flexible member to be manipulated by using the first manipulation element, a second manipulation element that inputs a second variable and a second selecting unit that selects a flexible member to be manipulated by using the second manipulation element. The control device includes a plurality of input selecting units corresponding to the plurality of flexible members. Each of the plurality of input selecting units outputs the first variable as a first signal when the corresponding flexible member is driven by using the first variable only, outputs a second signal obtained by time-integrating the second manipulated variable when the corresponding flexible member is driven by using the second variable only, and outputs a sum of the first signal and the second signal when the corresponding flexible member is driven by using the first variable and the second variable.

In one embodiment, at least one of the first, second, third and fourth manipulation elements of the input device may comprise a homing mechanism. In yet another embodiment, the input device includes a switch that invalidates an input from at least one of the first, second, third, and fourth manipulation elements. By way of example and without limitation, the first, second, third, and fourth manipulation element may comprise a joystick. In yet another embodiment, the transmission mechanism includes a wire that is wound around an output shaft of the drive source. Rotation of the drive source causes the wire to be pulled and the flexible member to bend.

In yet another aspect of the invention, a system comprising manipulator including a flexible member, an input device, and a control device is provided. The flexible member is connected to a first drive transmission mechanism and a second drive transmission mechanism bending the manipulator in a first direction and a second direction, respectively. The input device includes a first manipulation element that inputs a first variable for driving the flexible member in the first direction, a second manipulation element that inputs a second variable for driving the flexible member in the first direction, a third manipulation element that inputs a third variable for driving the flexible member in the second direction, and a fourth manipulation element that inputs a fourth variable for driving the flexible member in the second direction.

The control device including a first integrator that time-integrates the second manipulated variable, a first adder that adds an output of the first integrator and the first manipulated variable, a second integrator that time-integrates the fourth manipulated variable, and a second adder that adds an output of the second integrator and the third manipulated variable to calculate driving amounts to be provided to first and second drive sources. The first and second drive sources apply a driving force based on the calculated driving amounts to the first and second drive transmission mechanism, respectively, to bend the member.

Further features of the present invention will become apparent from the following description of exemplary embodiments with reference to the attached drawings.

BRIEF DESCRIPTION OF THE DRAWINGS

The accompanying drawings, which are incorporated herein and form part of the specification, illustrate various embodiments of the present invention. In the drawings, like reference numbers indicate identical or functionally similar elements. Additionally, the left-most digit(s) of a reference number identifies the drawing in which the reference number first appears.

FIG. 5 is a block diagram of a manipulator control device according to the first embodiment of the present invention.

FIG. 6A illustrates graphs representing angle and angular velocity inputs over a time interval according to one embodiment of the present invention.

FIG. 6B illustrates a graph representing a target angle over a time interval, the target angle calculated by the control device according to FIG. 5 based on the angle and angular velocity inputs according to FIG. 6A.

FIG. 13 illustrates a flexible element (bend) according to the fourth embodiment of the present invention in the Cartesian coordinate system.

FIGS. 14A-C demonstrate schematic diagrams presenting motion modes of the flexible member according to the fourth embodiment of the present invention.

DETAILED DESCRIPTION OF PREFERRED EMBODIMENTS

The present invention relates to a method and system including at least one input device, a control device, and a manipulator having at least one flexible member (bend). Specifically, an operator provides an input to the input device in communication with the control device. The control device calculates the motion of the at least one flexible member. According to one embodiment of the present invention, an angle input unit and an angular velocity input unit are provided in communication with the control device. The angle input unit is provided to input a first variable defining variation from the current bend shape. The angular velocity input unit is provided to input a second variable defining a variation in the bend shape per time unit. Another embodiment of the present invention is directed to the angle manipulation element (for example, a first joystick) having a homing mechanism so that when the operator releases the angle manipulation element to return to a home (neutral or zero) position corresponding to a "zero" input, the shape of the bend can automatically return to the shape that the bend had prior to the manipulation. When the homing mechanism is used for the angular-velocity manipulation element (for example, a second joystick), the operator releases the manipulation element to return to a home (neutral or zero) position and the bend automatically stops moving. In yet another embodiment of the present invention, the two manipulation elements (first and second joysticks) can be alternatively used. In this case, even when an operator unintentionally uses one of the manipulation elements (joysticks), the bend does not move. Accordingly, by selecting the angle manipulation element (first joystick) or angular-velocity the manipulation element (second joystick), the operator can select whether the shape of the bend automatically returns to the shape before the manipulation or the bend maintains the current shape. In yet another embodiment of the present invention, a manipulator including a plurality of bends is provided. In addition, a manipulator including a bend that is bendable in three dimensions is described below.

Figure 1:
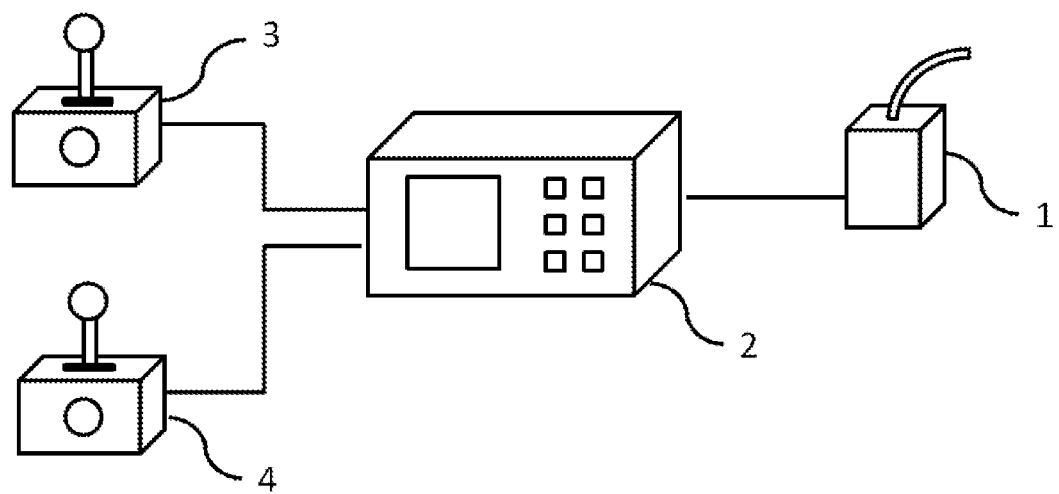
FIG. 1 is a schematic diagram illustrating a manipulator system according to a first embodiment of the present invention.

A wire-driven manipulator including a flexible member (bend) is provided in a first embodiment of the present invention. FIG. 1 illustrates a schematic diagram of a manipulator system including a manipulator 1, a control device 2, a first input unit 3, and a second manipulated-variable input unit 4. In one embodiment, the first input unit 3 and the second input unit 4 include respective joysticks each having a shaft. Each joystick outputs a variable as a function of time in accordance with the joystick's position relative to the neutral (zero or home) state. The control device 2 calculates and outputs a drive command to the manipulator 1 by applying different control laws to the variables outputted from the input units 3 and 4.

Figure 2:
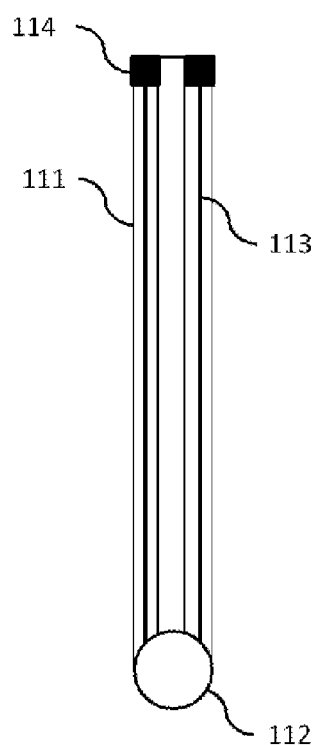
FIG. 2 is a schematic diagram of a wire-driven manipulator according to the first embodiment.

FIG. 2 illustrates the structure of the manipulator 1 of FIG. 1. The manipulator 1 includes a flexible member (bend) 111, a wire 113, and a drive source 112 that applies a driving force to the bend 111. In one embodiment, the bend 111 is hollow and can guide, for example, a forceps and/or a cleaning instrument. In some exemplary embodiments, the drive source 112 is a motor, including a shaft drive, gear motor, ultrasonic motor, etc. The drive source is able to apply a drive force to the driving-force transmitting mechanism in the form of the wire 113. For instance, the drive force may be applied through a rotational motion causing the wire or cable (the driving-force transmitting mechanism) 113 to move forwards and backwards thereby bending the flexible element 111. In another embodiment, the drive force is provided through linear motion instead of rotation. In yet another embodiment, the drive source 112 is provided with an encoder that detects rotational angles of the drive source 212 and a position control apparatus (not shown) that controls the rotational angles.

Specifically, in FIG. 2, the wire 113, which corresponds to a drive transmission mechanism, is wound around the output shaft of the drive source 112. The wire 113 is secured at stationary portions 114 attached to the flexible member 111. Accordingly, rotation of the drive source 112 causes the wire 113 to be pulled and the flexible member 111 to bend.

Figure 3:
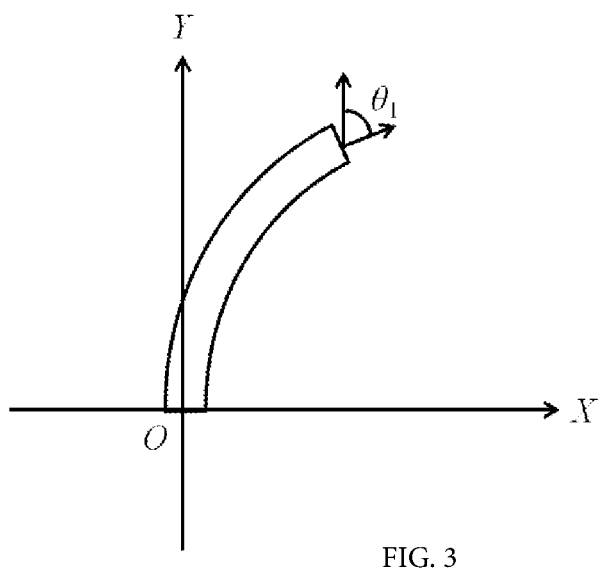
FIG. 3 illustrates a flexible element (bend) according to the first embodiment of the present invention in the Cartesian coordinate system.

FIG. 3 illustrates the flexible member 111 according to the first embodiment of the present invention positioned in the Cartesian coordinate system. As illustrated in FIG. 3, the longitudinal direction of the flexible member 111 corresponds to the Y-axis, and the radial direction corresponds to the X-axis. The flexible member 111 bends only in the XY plane. An angle formed between the flexible member 111 defined by a normal vector to the cross-section of the flexible member and the Y-axis is denoted by $\theta_1$. The angle $\theta_1$ defining the shape of the bend and the rotational angle $\varphi_1$ of the drive source 112 are proportional to the amount of the wire 113 which was pulled, and the relationship between the angle $\theta_1$ and the rotational angle $\varphi_1$ is expressed by formula (1):

$$\theta_1 = c_1 \varphi_1, \tag{1}$$

wherein $c_1$ is a constant.

Figure 4:
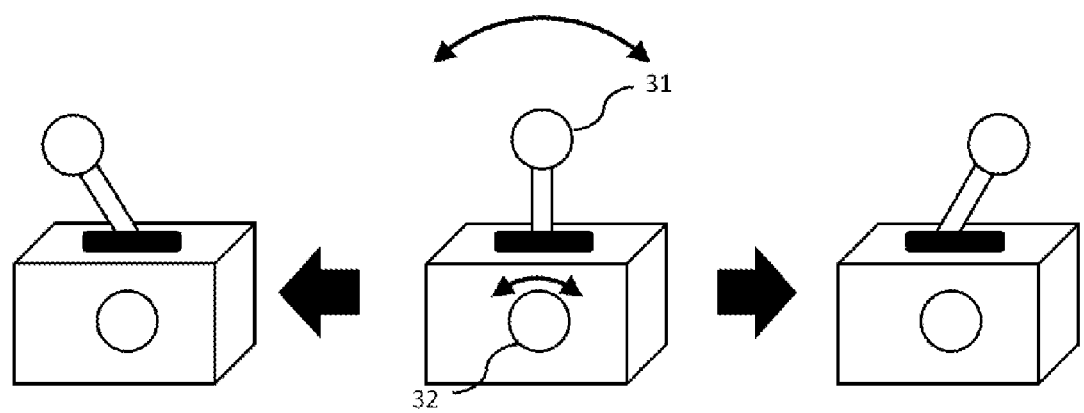
FIG. 4 is a schematic diagram illustrating an input device having a joystick moving between different positions.

FIG. 4 illustrates the first input unit 3 as shown in FIG. 1. The first input unit 3 includes a joystick 31 having one degree of freedom to be tilted from side to side and a dial 32. When the operator tilts the joystick 31 to the left-hand side, the first input unit 3 outputs a first variable $\Delta m_1$ proportional to the tilt angle of the joystick 31. When the joystick 31 is tilted by the same angle to the right-hand side, the first input unit 3 outputs a variable having the same magnitude as in the case where the joystick 31 is tilted to the left-hand side, but having the opposite sign. In one embodiment, the joystick 31 may include a rotary spring (not illustrated). When the operator releases the joystick, the restoring force of the spring causes the joystick 31 to return to the neutral (zero, home, central, vertical) position setting the first variable $\Delta m_1$ to zero. When the operator rotates the dial 32, the first input unit 3 outputs a first gain coefficient $\alpha_1$ proportional to the rotational angle of the dial 32. Similarly, the second input unit 4 includes a joystick 41 and a dial 42. The second input unit 4 outputs a second variable $\Delta m_2$ proportional to the tilt angle of the joystick 41 and a second gain coefficient $\alpha_2$ proportional to the rotational angle of the dial 42.

FIG. 5 is a block diagram of the control device 2 according to the first embodiment of the present invention. As illustrated in FIG. 5, the control device 2 includes a first variable converter 211, a second variable converter 212, an integrator 22, an adder 23, and an angle calculator 24. The first variable converter 211 multiplies the first variable $\Delta m_1$ by the first gain coefficient $\alpha_1$ ($\Delta m_1$ and $\alpha_1$ inputted from the input unit 3) and outputs a first angle $\Delta \theta_1$ expressed by formula (2):

$$\Delta \theta_1 = \alpha_1 \Delta m_1 \tag{2}$$

It can be seen from formula (2) that the first variable $\Delta m_1$ corresponds to the target angle of the bend. Similarly, the second variable converter 212 multiplies the second manipulated variable $\Delta m_2$ by the second manipulation gain $\alpha_2$ ($\Delta m_2$ and $\alpha_2$ inputted from the input unit 4) and outputs the angular velocity command $\Delta \dot{\theta}_2$ expressed by formula (3):

$$\Delta \dot{\theta}_2 = \alpha_2 \Delta m_2 \tag{3}$$

The integrator 22 outputs the second angle command $\Delta \theta_2$ obtained by integrating the angular velocity $\Delta \dot{\theta}_2$ over time and expressed by formula (4):

$$\Delta \theta_2 = \int \Delta \dot{\theta}_2 dt \tag{4}$$

$$= \alpha_2 \int \Delta m_2 dt$$

It can be seen from formula (4) that the second variable $\Delta m_2$ corresponds to the target angular velocity of the bend. The adder 23 adds the first angle command $\Delta\theta_1$ and the second angle command $\Delta\theta_2$ and outputs the target angle $\theta_{ref1}$ expressed by formula (5):

$$\theta_{ref1}=\Delta\theta_1+\Delta\theta_2 \qquad (5)$$

The angle calculator 24 calculates the rotational angle $\varphi_{ref1}$ of the drive source from the angle target value $\theta_{ref1}$ by using formula (1).

Manipulator movement based upon calculations performed by the control device 2 in response to the joysticks 31 and 41 being manipulated is discussed below with reference to FIGS. 6A-B. According to the first embodiment of the present invention, the first gain coefficient $\alpha_1$ and the second gain coefficient $\alpha_2$ are 1. A dotted line and a dashed line in FIG. 6A represent operator inputs $\Delta m_1$ and $\Delta m_2$ through the input units 3 and 4, respectively, on the time interval [0; $t_{12}$]. FIG. 6B illustrates the target angle $\theta_{ref1}$ calculated according to equation (5) based on the operator inputs $\Delta m_1$ and $\Delta m_2$ according to FIG. 6A. According to the first embodiment, as illustrated in FIG. 6A, the first variable $\Delta m_1$ outputted by the joystick 31 is first increased at a constant rate between time 0 and time $t_1$. Subsequently, the first variable $\Delta m_1$ is maintained at a constant value between time $t_1$ and time $t_2$, and is decreased also at a constant rate between $t_2$ and $t_3$ until the joystick 31 returns to the initial zero position at time $t_3$. Subsequently, the same manipulation is performed on the joystick 41 (second variable $\Delta m_2$) between time $t_4$ and time $t_7$. Then, the joystick 31 (first variable $\Delta m_1$) is manipulated between time $t_8$ and time $t_{11}$ in the same manner as during the interval from 0 to $t_3$. As expressed by formula (2), when the first gain coefficient $\alpha_1$ is 1, the first angle command $\Delta\theta_1$ and the first variable $\Delta m_1$ are equal. The second variable $\Delta m_2$ is zero between time 0 and time $t_3$, and accordingly, as illustrated in FIGS. 6A-B, the angle target value $\theta_{ref1}$ is equal to the first variable $\Delta m_1$ during the same time period.

Accordingly, the target angle (angle target value) $\theta_{ref1}$ of the bend increases at a constant rate between time 0 and time $t_1$, and the target angle $\theta_{ref1}$ is constant between time $t_1$ and time $t_2$. The target angle $\theta_{ref1}$ decreases at a constant rate from time $t_2$ and becomes zero at time $t_3$. Thus, in the case of manipulation of the joystick 31, the angle of the bend can return to the angle before manipulation in a manner in which the joystick is returned to the initial (zero, neutral, home) location. As expressed by formula (4), the second angle command $\Delta\theta_2$ is proportional to the integral of the second variable $\Delta m_2$, and accordingly, when the variable of the joystick 41 is increased between time $t_4$ and time $t_5$, the angular velocity of the bend increases. The angular velocity stays constant between time $t_5$ and time $t_6$, during which the variable $\Delta m_2$ of the joystick 41 is constant, and the angular velocity decreases between time $t_6$ and time $t_7$, during which the variable $\Delta m_2$ decreases.

As illustrated in FIGS. 6A-B, the target angle of the bend $\theta_{ref1}$ is not zero at time $t_7$, at which the variable $\Delta m_2$ of the joystick 41 is zero. Thus, in the case of manipulation of the joystick 41, the target angle of the bend $\theta_{ref1}$ does not return to the angle before manipulation even when the joystick is returned to the initial (zero, neutral, home) position. When the joystick 31 is manipulated again between time $t_8$ and time $t_{11}$, the target angle of the bend $\theta_{ref1}$ increases first and subsequently returns again to the angle before manipulation, from the same consideration. For these reasons, the first variable input unit 3 is suitable for manipulation to temporarily change the shape (configuration) of the bend. This function makes the manipulation easier to observe a vicinity area around the target point by allowing the angle of the bend to direct the target point quickly. In particular, since the joystick 31 according to the first embodiment has a homing function that uses the rotary spring, the return manipulation can be performed in a manner in which an operator merely releases the joystick 31. When the bend is manipulated by using the second input unit 4, the angle of the bend is maintained even when the manipulated variable of the joystick 41 is returned to the neutral (home, zero, initial) position. For this reason, the second input unit 4 is suitable for permanently changing the shape of the bend. Since the joystick 41 also has a homing function that uses a rotary spring, the bend can be stopped in a manner in which the operator merely releases the joystick 41. This prevents the bend from moving as a result of an operator failing to return the joystick into the neutral ("zero" or "home") position and from coming into unintentional contact with an organ. Thus, the shape of the bend is controlled such that the second input unit 4 is used to avoid contact with an organ while the first input unit 3 is used to observe the surroundings.

Figure 7:
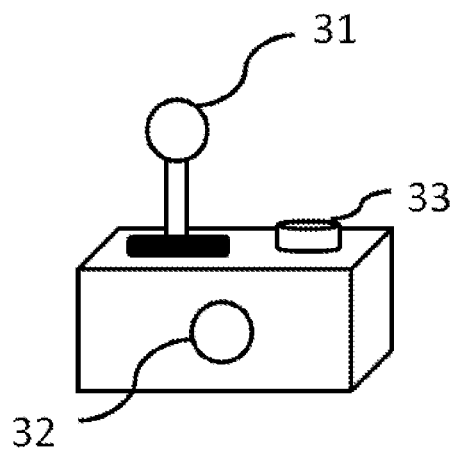
FIG. 7 is a schematic diagram of an input device according to a second embodiment of the present invention.

A system according to a second embodiment of the present invention includes exclusive use of either the first input unit 3 or the second input unit 4. FIG. 7 is a schematic diagram of the first input unit 3 according to the second embodiment of the present invention. The input unit 3 according to the second embodiment differs from the first input unit 3 according to the first embodiment in including a switch 33. When the operator pushes the switch button 33, the state $s_1$ of the switch 33 alternates between the ON and OFF state. Similarly, the second input unit 4 according to the second embodiment includes a switch 43. When the operator pushes the switch 43, the state $s_2$ of the switch 43 alternates between the ON and OFF state. The states $s_1$ and $s_2$ are outputted to the control device 2.

Figure 8:
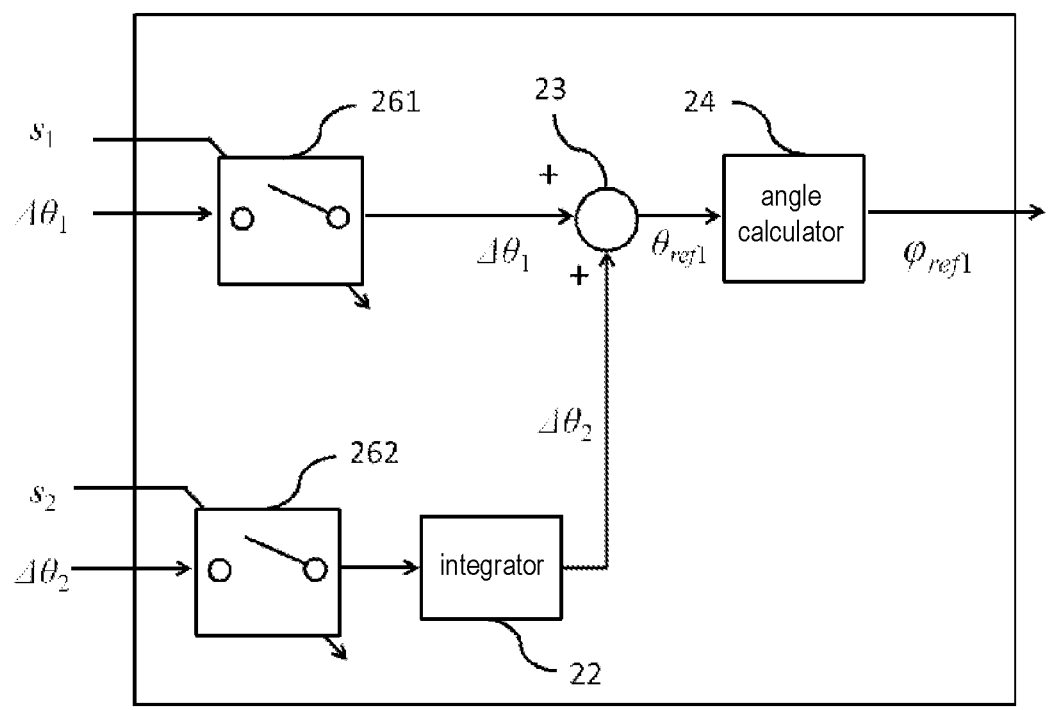
FIG. 8 is a block diagram of a manipulator control device according to the second embodiment of the present invention.

FIG. 8 is a block diagram of the control device 2 according to the second embodiment of the present invention. The control device 2 according to the second embodiment differs from the control device 2 according to the first embodiment in including a first switch 261 and a second switch 262. According to the second embodiment, operator's input is converted according to equations (2) and (3) which is the same as in the first embodiment. The first switch 261 reads the state $s_1$ of the switch 33 and transmits the first angle command $\Delta\theta_1$ to the adder 23 when $s_1$ is in the ON state. The first switch 261 blocks the first angle command $\Delta\theta_1$ when $s_1$ is in the OFF state. Similarly, the second switch 262 reads the state $s_2$ of the switch 43 and transmits the angular velocity command $\Delta\dot{\theta}_2$ to the integrator 22 when $s_2$ is in the ON state. The second switch 262 blocks the angular velocity command $\Delta\dot{\theta}_2$ when $s_2$ is in the OFF state. For these reasons, when $s_1$ is in the ON state and $s_2$ is in the OFF state, the target angle $\theta_{ref1}$ depends on only the input from the first input unit 3. When $s_1$ is in the OFF state and $s_2$ is in the ON state, the target angle $\theta_{ref1}$ depends only on the input from the second input unit 4. Accordingly, the first input unit 3 and the second input unit 4 can be alternatively used in the manner when either the state of the switch 33 or the state of the switch 43 is changed to the ON state.

Thus, even when the operator unintentionally touches the first manipulation element (joystick), the first manipulation element is disabled and doesn't change the angle of the bend.

As described above, the first input unit 3 can input the first variable $\Delta m_1$ corresponding to the target angle of the bend. However, the joystick 31 has the homing function and is not suitable for manipulation to permanently change the shape of the manipulator. In view of this, a manipulation system according to a third embodiment is provided to enable the operator to input the target angle of the bend and constantly maintain the shape of the manipulator.

Figure 9:
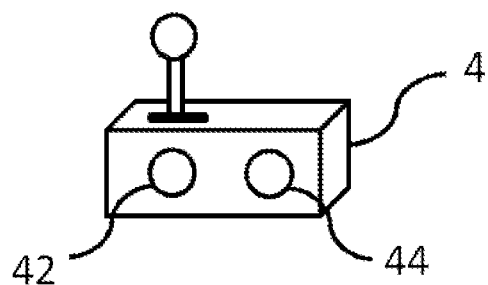
FIG. 9 is a schematic diagram of an input device according to a third embodiment of the present invention.

FIG. 9 is a schematic diagram of the second input unit 4 according to the third embodiment of the present invention. The second input unit 4 according to the third embodiment differs from the second input unit 4 according to the first embodiment in including a dial 44. When the operator rotates the dial 44, the dial 44 outputs a third manipulated variable $\Delta m_3$ proportional to the rotational angle of the dial 44.

Figure 10:
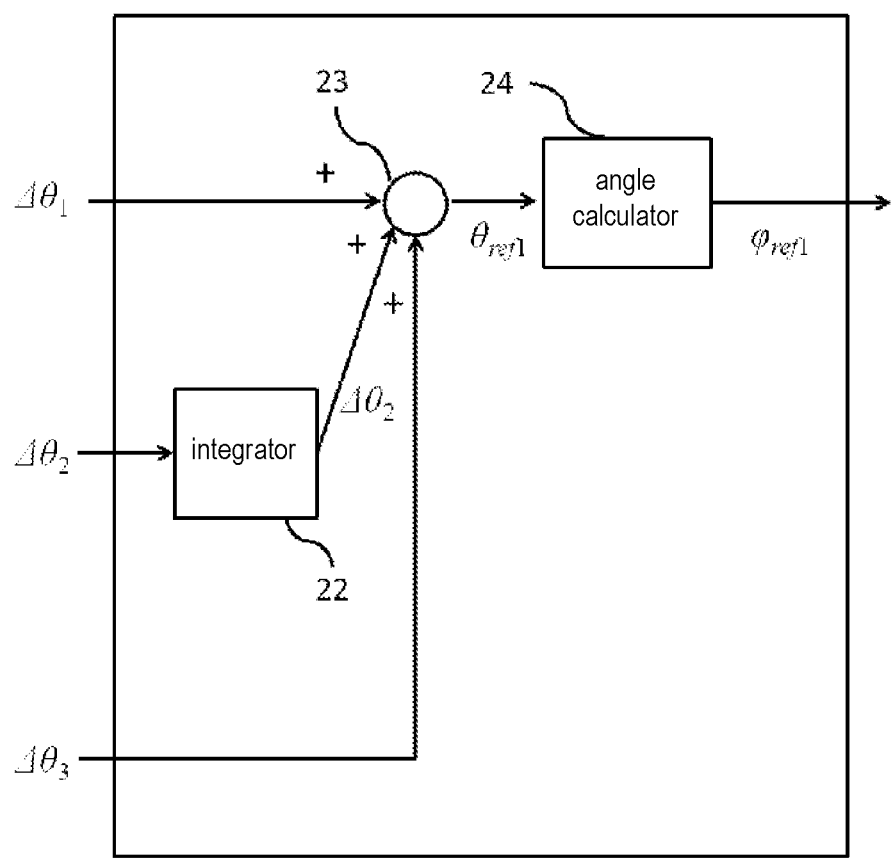
FIG. 10 is a block diagram of a manipulator control device according to the third embodiment of the present invention.

FIG. 10 is a block diagram of the control device 2 according to the third embodiment. The third variable $\Delta m_3$ is inputted from the dial 44 to a third converter (not illustrated) analogous to converters 211 and 212 as shown in FIG. 5. The third converter calculates a third angle command $\Delta \theta_3$ by multiplying the third variable $\Delta m_3$ by a constant and outputs the third angle $\Delta \theta_3$. The adder 23 adds the first angle $\Delta \theta_1$, the second angle $\Delta \theta_2$, and the third angle $\Delta \theta_3$ to calculate the target angle $\theta_{ref1}$. The angle calculator 24 calculates the rotational angle ($\varphi_{ref1}$ of the drive source 112 (FIG. 2) from the target angle $\theta_{ref1}$ by using formula (1) and outputs the calculated rotational angle $\varphi_{ref1}$. Accordingly, the dial 44 enables the operator to directly input the target angle of the bend and maintain the shape of the bend after manipulation even when the operator releases the manipulation elements (joysticks).

In yet another embodiment, a function is added to input a user-defined angle of the bend corresponding to the home (zero, neutral) position of the first input unit 3. The operator can set an angle of the bend during the manipulation as the angle corresponding to the home position of the first input unit 3 by using the second input unit 4. Since the home position of the first input unit 3 is changed to the user-defined angle, the operator can easily return the angles of the bend to the user-defined angle by only releasing the joystick 31.

With increase in the number of the bends, the shape of the manipulator undergoes more complex changes making manipulation more difficult. In view of this, the control device according to a fourth embodiment of the present invention is used for a manipulator including a plurality of bends.

Figure 11:
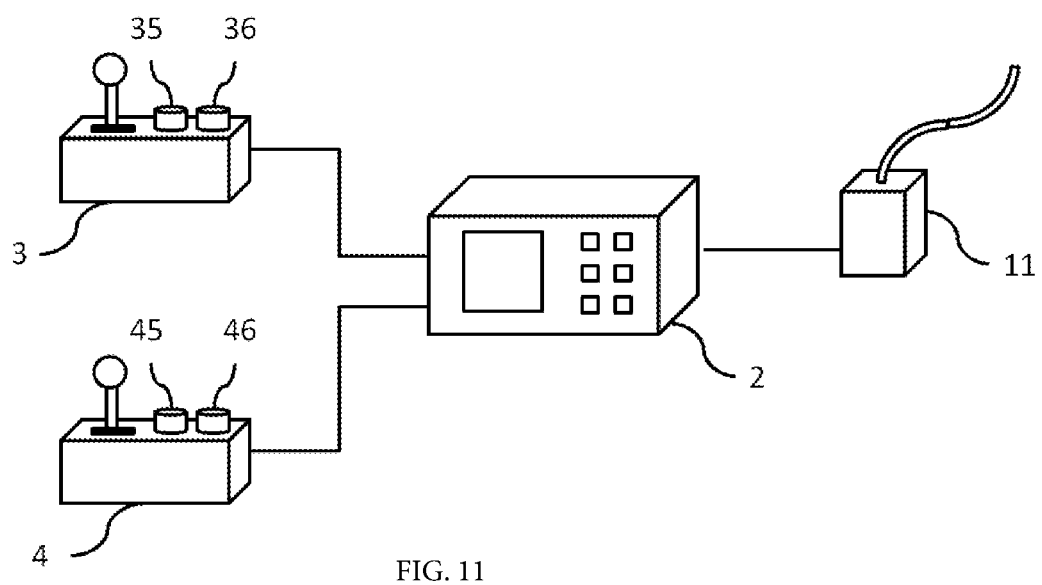
FIG. 11 is a schematic diagram illustrating a manipulator system according to a fourth embodiment of the present invention.

FIG. 11 is a schematic diagram of a manipulator-operating system according to the fourth embodiment of the present invention. The fourth embodiment of the present invention is directed to a manipulator including two bends that can be driven independently of each other. The first input unit 3 includes switches 35 and 36. The operator uses the switches 35 and 36 to select the bend of the manipulator of FIG. 12 to be manipulated by using the input unit 3. Similarly, the second input unit 4 includes switches 45 and 46 to select the bend of the manipulator of FIG. 12 to be manipulated by using the input unit 4.

Figure 12:
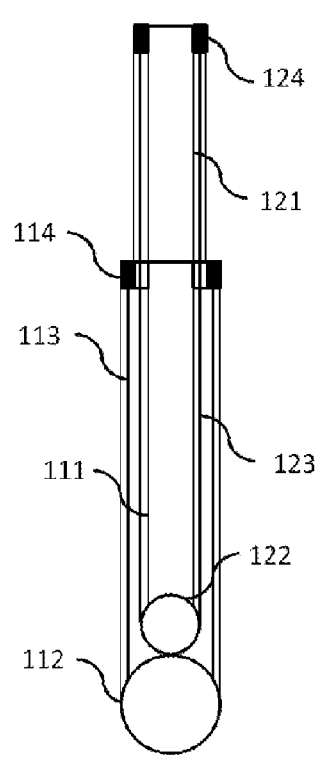
FIG. 12 is a schematic diagram of a wire-driven manipulator having two flexible elements according to the fourth embodiment of the present invention.

FIG. 12 illustrates the structure of the manipulator according the forth embodiment of the present invention. The manipulator includes a first bend at the drive source side of the manipulator and a second bend at the end side of the manipulator. Each bend has the same structure as that of the manipulator according to the first embodiment of the present invention (FIG. 2). Specifically, the output shaft of the drive source 112 of the first bend is connected to stationary portions 114 with a wire 113 interposed there between. Rotation of the drive source 112 causes the flexible member 111 to bend. Similarly, the output shaft of a drive source 122 of the second bend is connected to stationary portions 124 with a wire 123 interposed there between. Rotation of the drive source 122 causes a flexible member 121 to bend.

FIG. 13 illustrates the manipulator according to the fourth embodiment of the present invention in the Cartesian coordinate system. The radial direction of the flexible member 111 corresponds to the X-axis, and the longitudinal direction corresponds to the Y-axis. The angle formed between the end of the first bend and the Y-axis is denoted by $\theta_1$, and the angle formed between the end of the second bend and the Y-axis is denoted by $\theta_2$. The angle defining the end of each bend depends only on the driving amount of the wire connected thereto and does not depend on the angle of the other bend. The driving amount of each wire is proportional to the rotational angle of the corresponding drive source 112 and 122. For this reason, the relationships between the angles $\theta_1$ and $\theta_2$ of the bends and the rotational angles $\varphi_1$ and $\varphi_2$ of the drive sources 112 and 122 are expressed as:

$$\theta_1 = c_1 \varphi_1 \qquad (6)$$

$$\theta_2 = c_2 \varphi_2, \qquad (7)$$

wherein $c_1$ and $c_2$ are constants.

The following description includes characteristic movement of the manipulator according to the fourth embodiment of the present invention in the case where one of the drive sources is appropriately selected. When only the drive source 122 is driven, as illustrated in FIG. 14A, the shape of the first bend does not change, but the second bend bends. Accordingly, this mode is suitable to control the shape of each bend such that the bend avoids touching an organ present in the direction in which the manipulator is inserted. When only the drive source 112 is driven, as illustrated in FIG. 14B, the position of the end of the second bend can be changed while the direction of the end of the second bend stays the same. Accordingly, this mode (hereinafter referred to as angled view mode) is suitable to move the position of observation along a wall surface, such as a stomach wall or an intestinal wall. When the drive source 112 and the drive source 122 are driven in the same direction, as illustrated in FIG. 14C, the position of the end of the manipulator can be substantially changed. Accordingly, this mode (hereinafter referred to as bending mode) is suitable to observe the body over a wide range of locations or to move the end of the manipulator in order to avoid contact with an organ. The manipulator operating system according to the fourth embodiment can switch between these movement patterns by using the switches 35, 36, 45, and 46 as described above and shown in FIG. 11. For example, this enables the operator to select the angled view mode or the bending mode in accordance with the surgery or diagnostic procedure performed by the operator.

Figure 15:
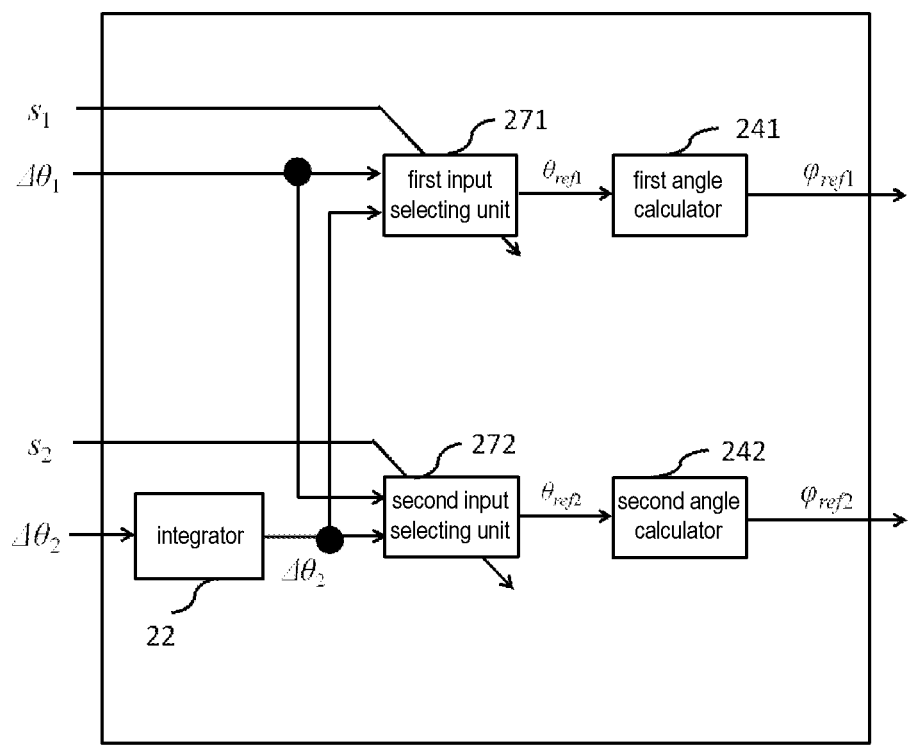
FIG. 15 is a block diagram of a manipulator control device according to the fourth embodiment of the present invention.

FIG. 15 is a block diagram of the control device 2 according to the fourth embodiment. The control device 2 according to the fourth embodiment includes input selecting units 271 and 272 that calculate the target angle $\theta_{ref1}$ of the first bend and the target angle $\theta_{ref2}$ of the second bend based on the state of the switches 35, 36, 45, and 46 of the input units 3 and 4. The first input selecting unit 271 adds the first angle $\Delta \theta_1$ and the second angle $\Delta \theta_2$ and outputs the sum thereof as the first angle target value $\theta_{ref1}$ when both the switch 35 and the switch 45 are in the ON state. The first input selecting unit 271 outputs the first angle target value $\theta_{ref1}$ as the first angle command $\Delta \theta_1$ when only the switch 35 is in the ON state and outputs the first angle target value $\theta_{ref1}$ as the second angle command $\Delta \theta_2$ when only the switch 45 is in the ON state. Similarly, the second input selecting unit 272 adds the first angle $\Delta \theta_1$ and the second angle $\Delta \theta_2$ and outputs the sum thereof as the second target angle $\theta_{ref2}$ when the switch 36 and the switch 46 are in the ON state. The second input selecting unit 272 outputs, as the second angle target value $\theta_{ref2}$, the first angle $\Delta\theta_1$ when only the switch 36 is in the ON state and outputs, as the second angle target value $\theta_{ref2}$, the second angle $\Delta\theta_2$ when only the switch 46 is in the ON state. A first angle calculator 241 and a second angle calculator 242 calculate the rotational angles $\varphi_{ref1}$ and $\varphi_{ref2}$ based on the angle target values $\theta_{ref1}$ and $\theta_{ref2}$ by using formula (6) and formula (7), respectively.

The control devices according to the fourth embodiment, as described above, are used for manipulators that bend in a single specific plane. However, sometimes it is preferable that the insertion portion of a manipulator bends in three dimensions along the passage so that each manipulator enters the body while avoiding contact with organs. For this reason, a control device according to a fifth embodiment of the present invention is provided to control a manipulator bendable in three dimensions.

Figure 16:
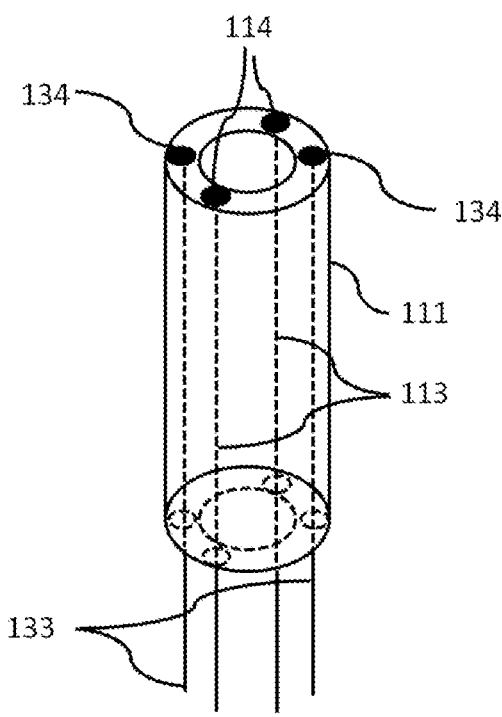
FIG. 16 is a schematic diagram of a three-dimensional manipulator according to a fifth embodiment of the present invention.

FIG. 16 illustrates a manipulator according to the fifth embodiment. The manipulator includes wires 113 and 133 corresponding to two orthogonal planes, respectively. The wire 113 is terminated to the output shaft of the first drive source (not illustrated) and the ends of the wire 113 are secured to the flexible member 111 by using the stationary elements 114. Similarly, the wire 133 is terminated to the output shaft of the second drive source (not illustrated) and the ends of the wire 133 are secured to the flexible member 111 by using stationary elements 134. In this case, when only the first drive source is driven, the manipulator bends along a plane on which the wire 113 extends. When only the second drive source is driven, the manipulator bends along a plane on which the wire 133 extends. When the first drive source and the second drive source are driven at the same time, the manipulator bends along a plane different from that in the case where the first drive source or the second drive source is driven alone.

In some embodiments, the flexible member is a multi-segmented robot having multiple deformation sections. Thus, the flexible member may comprise 2, 3, 4, 5, 6 or more deformation sections, where the bending of each deformation section may be controlled via a transmission mechanism. For example, each deformation section may be controlled by two or more wires terminating at the distal end of the deformation sections. In other examples, the system as presented herein may contain a manipulator having multiple deformation sections as described in U.S. patent application Ser. No. 15/901,599, which is herein incorporated by reference in its entirety.

Figure 17:
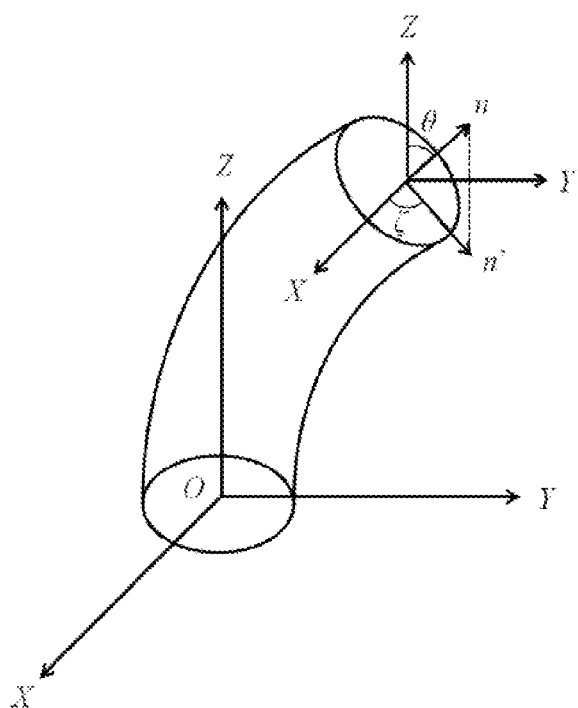
FIG. 17 illustrates a manipulator flexible member (bend) according to the fifth embodiment in the Cartesian coordinate system.

FIG. 17 illustrates the manipulator according to the fifth embodiment of the present invention in the Cartesian 3-D coordinate system. Specifically, the longitudinal direction of the manipulator corresponds to the Z-axis. The plane along which the manipulator bends when the first drive source is driven corresponds to the XZ plane, and the plane along which the manipulator bends when the second drive source is driven corresponds to the YZ plane. A vector representing the direction of an end portion of the manipulator is denoted by n. An angle formed between the vector n and the Z-axis is denoted by $\theta$ ($\theta$ is referred to below as a bend angle). An angle formed between a vector n' obtained by projecting the vector n on the XY plane and the X-axis is denoted by $\zeta$ ($\zeta$ is referred to below as a turning angle). The turning angle $\zeta$ represents the rotational angle of the plane (referred to below as a drive plane) along which the manipulator bends from the XZ plane. The bend angle represents the magnitude of the bend of the manipulator along the drive plane. The bend angle $\theta$ and the turning angle $\zeta$ depend on the driving amount of the wire 113 and the wire 133. The driving amount of each wire is proportional to the rotational angle of the drive source connected to the wire. Accordingly, the bend angle $\theta$ and the turning angle $\zeta$ can be expressed as:

$$\theta = F_\theta(\varphi_1, \varphi_3) \tag{8}$$

$$\zeta = F_\zeta(\varphi_1, \varphi_3), \tag{9}$$

by using functions $F_\theta$ and $F_\zeta$ where $\varphi_1$ and $\varphi_3$ represent the rotational angle of the first drive source and the rotational angle of the second drive source respectively. Accordingly, turning movement suitable for the insertion of the manipulator and observation of the surroundings can be performed in a manner in which the rotational angles $\varphi_1$ and $\varphi_3$ are appropriately selected. For example, in the case where there is an organ on a plane, the turning angle $\zeta$ is increased or decreased and the drive plane is controlled such that the plane is avoided. This enables the manipulator to be inserted without contact with the organ. In addition, observation can be made in a wide area in the radial direction of the manipulator in a manner in which the bend angle $\theta$ is kept constant and the turning angle $\zeta$ is changed. The turning movement is thus effective for both the insertion of the manipulator and observation. Accordingly, regarding the turning movement as in the bending movement, the operability is improved in the case where the angle and the angular velocity can be selectively inputted in accordance with procedure objectives.

Figure 18:
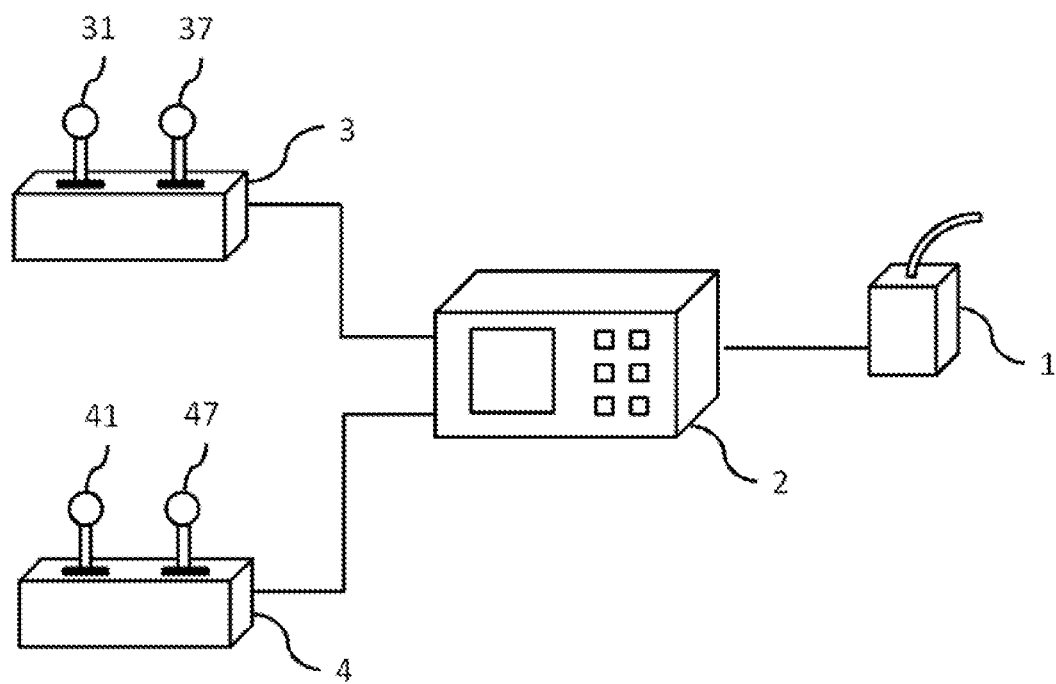
FIG. 18 is a schematic diagram illustrating a manipulator system according to the fifth embodiment.

FIG. 18 illustrates a manipulator-operating system according to the fifth embodiment that can perform the bending movement and the turning movement based on the inputted angle and angular velocity. The first input unit 3 according to the fifth embodiment includes the joystick 31 that inputs a bend angle and the joystick 37 that inputs a turning angle. When the operator manipulates the joystick 31 and the joystick 37, the first input unit 3 outputs a bend angle $\Delta\theta_1$ and a turning angle $\Delta\zeta_1$ that are proportional to the input variables. Similarly, the second input unit 4 includes the joystick 41 that inputs a bend angular velocity and a joystick 47 that inputs a turning angular velocity. When these joysticks are tilted, the second input unit 4 outputs a bend angular velocity $\Delta\dot\theta_2$ and a turning angular velocity $\Delta\dot\zeta_2$ that are proportional to the input variables.

Figure 19:
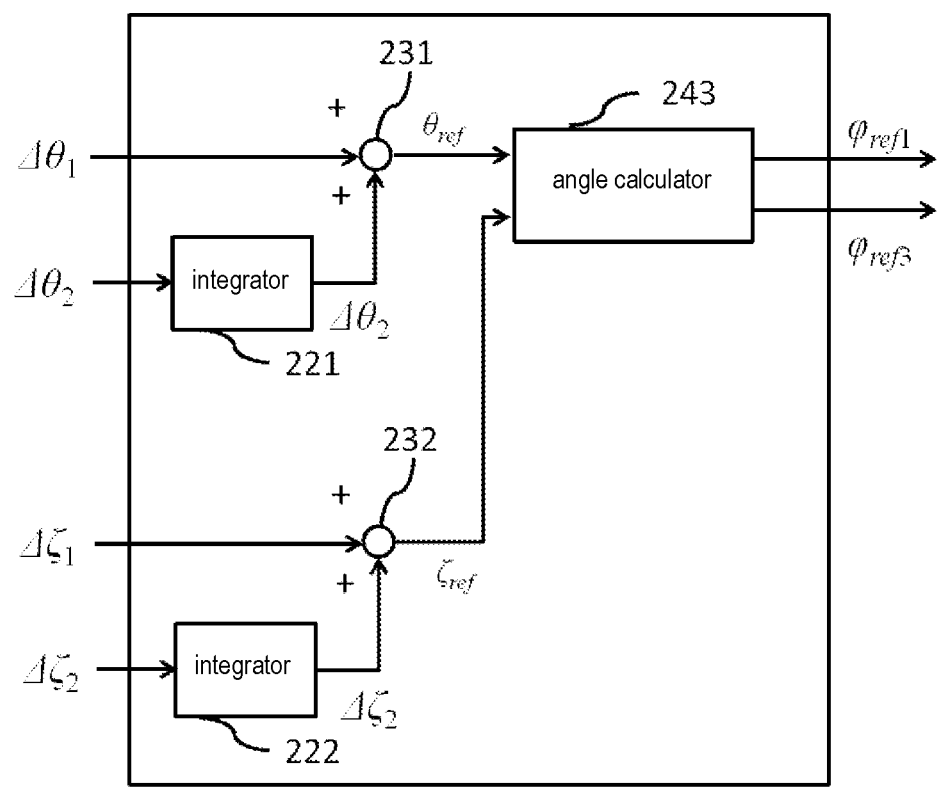
FIG. 19 is a block diagram of a manipulator control device according to the fifth embodiment.

FIG. 19 is a block diagram of the control device 2 according to the fifth embodiment of the present invention. An integrator 221 calculates the bend angle $\Delta\theta_2$ by integrating the bend angular velocity command $\Delta\dot\theta_2$. An adder 231 calculates a bend angle target value $\theta_{ref}$ by adding the bend angle $\Delta\theta_1$ and the bend angle $\Delta\theta_2$. Similarly, an integrator 222 calculates a turning angle $\Delta\zeta_2$ by integrating the turning angular velocity $\Delta\dot\zeta_2$. An adder 232 outputs a turning angle target value $\zeta_{ref}$ obtained by adding the turning angle $\Delta\zeta_2$ and the turning angle $\Delta\zeta_2$. An angle calculator 243 calculates the angles $\varphi_{ref1}$ and $\varphi_{ref3}$ of the drive sources from the bend angle target value $\theta_{ref}$ and the turning angle target value $\zeta_{ref}$ by using formula (8) and formula (9) and outputs the angles $\varphi_{ref1}$ and $\varphi_{ref3}$. This enables the angle and the angular velocity to be selectively inputted in accordance with the purpose of manipulation in the case of the turning movement.

The control devices according to the present invention can be used for a flexible manipulator including bends that are bendable in three dimensions. For example, a system may include, at every node, the input device for the bending or turning manipulation according to the fifth embodiment. The input units and the input selecting units may be used to switch the bends to be driven according to the fourth embodiment.

In examples, as described above, the wire wound around the drive source is used as the transmission mechanism to bend the flexible member. The transmission mechanism, however, is not limited to the embodiments as described above. For example, in one embodiment, one of wound wires may be secured and the other wire may be driven. In yet another embodiment, the transmission mechanism may be pushed or pulled by using a direct drive mechanism.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions. The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While the subject matter of this disclosure has been described and shown in considerable detail with reference to certain illustrative embodiments, including various combinations and sub-combinations of features, those skilled in the art will readily appreciate other embodiments and variations and modifications thereof as encompassed within the scope of the present disclosure. Moreover, the descriptions of such embodiments, combinations, and sub-combinations is not intended to convey that the claimed subject matter requires features or combinations of features other than those expressly recited in the claims. Accordingly, the scope of this disclosure is intended to include all modifications and variations encompassed within the spirit and scope of the following appended claims.

The invention claimed is:

1. A system comprising:
a flexible member connected to a drive transmission mechanism;
at least one input device to cause bending of a segment of the flexible member, wherein the input device includes a first manipulation element provided to input a first variable changing over time, and a second manipulation element, wherein the first and second manipulation elements can be present on the same at least one input device or can be on separate input devices, wherein the second manipulation element is provided to input a second variable changing over time;
wherein, each of the first and second manipulation elements has a neutral position, and;
a processor including an integrator that time-integrates the second variable and an adder that adds an output of the integrator and the first variable with different coefficients to calculate a driving amount to apply to the drive transmission mechanism, wherein the driving amount is proportional to a bend angle $\theta$ formed between the flexible member and a vertical axis, $\theta = \alpha_1 \Delta m_1 + \alpha_2 \int \Delta m_2 dt$, where $\Delta m_1$, is the first variable defining an angle and $\Delta m_2$ is the second variable defining an angular-velocity; and
a drive source applying a driving force to the drive transmission mechanism based on the calculated driving amount to bend the flexible member, wherein the flexible member is caused to bend three-dimensionally with the bend angle $\theta$ and a turning angle $\zeta$;
wherein,
(i) when the first manipulation element is allowed to return to the neutral position, the bend of the flexible member is returned to a position of the flexible member prior to being acted on by the driving force; and
(ii) when the second manipulation element is allowed to return to the neutral position, the bend of the flexible member is not changed.

2. The system according to claim 1, wherein at least one of the first manipulation element and the second manipulation element of the at least one input device includes a homing mechanism.

3. The system according to claim 2, wherein the at least one input device includes a third manipulation element that inputs a third variable, wherein the first manipulation element or the third manipulation element include the homing mechanism, and wherein the processor includes an adder that adds the first variable and the third variable.

4. The system of claim 1, wherein the transmission mechanism includes a wire that causes the flexible member to bend when pulled.

5. The system of claim 4, wherein the wire is wound around an output shaft of the drive source and rotation of the drive source causes the wire to be pulled.

6. The system according to claim 1, wherein the at least one input device includes a switch that invalidates an input from at least one of the first manipulation element and the second manipulation element.

7. The system of claim 1, wherein at least one of the first and second manipulation elements comprises a joystick.

8. The system of claim 1, wherein the at least one input device includes dials to input coefficients to multiply the first and second variables.

9. The system of claim 1, wherein the flexible member comprises two or more separately bendable sections.

10. The system of claim 1, wherein the first manipulator element inputs the bend angle $\theta$ and the turning angle $\zeta$, and wherein the second manipulator element inputs a bend angle velocity and a turning angle velocity.

11. The system of claim 1, additionally comprising a first and second drive source connected to the first and second manipulation elements by means of a first and second wires, respectively, which first and second wires are extended from the first and second drive sources and connected to the flexible member;
wherein,
(i) when only the first drive source is driven, the flexible member bends along a plane on which the first wire extends;

(ii) when only the drive source is driven, the flexible member bends along a plane on which the second wire extends; and (iii) when the first and second drive sources are driven at the same time, the flexible member bends along a plane different from that in (i) and (ii).

12. The system of claim 1, wherein a desired bend of the flexible member is set as an angle corresponding to the neutral position of the first manipulation element by using the second manipulation element.

13. A method comprising:

providing a flexible member connected to a drive transmission mechanism to cause bending of a segment of the flexible member;

inputting a first variable changing over time and a second variable changing over time through first and second manipulation elements of at least one input device, respectively, wherein the first and second manipulation elements can be present on the same at least one input device or can be on separate input devices;

wherein, each of the first and second manipulation elements has a neutral position, and;

providing a processor to time-integrate the second manipulated variable and add an output of an integrator and the first variable with different coefficients to calculate a driving amount, wherein the driving amount is proportional to a bend angle $\theta$ formed between the flexible member and a vertical axis, $\theta = \alpha_1 \Delta m_1 + \alpha_2 \int \Delta m_2 dt$, defining an angular-velocity; and applying a driving force by a drive source, the drive force based on the calculated driving amount value to the drive transmission mechanism to bend the flexible member, wherein the flexible member is caused to bend three-dimensionally with the bend angle $\theta$ and a turning angle $\zeta$;

wherein, (i) when the first manipulation element is allowed to return to the neutral position, the bend of the flexible member is returned to a position of the flexible member prior to being acted on by the driving force; and (ii) when the second manipulation element is allowed to return to the neutral position, the bend of the flexible member is not changed.

14. The method of claim 13, wherein at least one of the first manipulation element and the second manipulation element of the at least one input device includes a homing mechanism.

15. The method of claim 13, wherein the transmission mechanism includes a wire that causes the flexible member to bend when pulled.

16. The method of claim 15, wherein the wire is wound around an output shaft of the drive source and rotation of the drive source causes the wire to be pulled.

17. The method of claim 13, wherein the at least one input device includes a switch that invalidates an input from at least one of the first manipulation element and the second manipulation element.

18. The method of claim 13, wherein the at least one input device includes a third manipulation element that inputs a third variable, wherein the first manipulation element or the third manipulation element include the homing mechanism, and wherein the processor includes an adder that adds the first variable and the third variable.

19. The method of claim 13, wherein the first and second manipulation element is a joystick.

20. The method of claim 13, wherein the at least one input device includes dials to input coefficients to multiply the first and second variables.

21. The method of claim 13, wherein the flexible member is caused to bend three-dimensionally by inputting a bend angle and a turning angle through the first manipulation element and inputting a bend angle velocity and a turning angle velocity through the second manipulation element.

22. The method of claim 13, additionally comprising providing a first and second drive source connected to the first and second manipulation elements by means of a first and second wires, respectively, which first and second wires are extended from the first and second drive sources and connected to the flexible member; and, bending the flexible member:

(i) along a plane on which the first wire extends when only the first drive source is driven;

(ii) along a plane on which the second wire extends when only the drive source is driven; and (iii) along a plane different from that in (i) and (ii) when the first and second drive sources are driven at the same time.

23. The method of claim 13, wherein a desired bend of the flexible member is set as an angle corresponding to the neutral position of the first manipulation element by using the second manipulation element.

* * * * *